United States Patent
Smith et al.

(10) Patent No.: US 9,945,775 B2
(45) Date of Patent: Apr. 17, 2018

(54) ACTIVE CHEMICAL SENSING USING OPTICAL MICROCAVITY

(71) Applicant: ISIS INNOVATION LIMITED, Oxford Oxfordshire (GB)

(72) Inventors: Jason Michael Smith, Oxford (GB); Claire Vallance, Oxford (GB)

(73) Assignee: ISIS INNOVATION LIMITED, Oxford, Oxfordshire (GB)

( * ) Notice: Subject to any disclaimer, the term of this patent is extended or adjusted under 35 U.S.C. 154(b) by 0 days.

(21) Appl. No.: 14/398,752

(22) PCT Filed: May 3, 2013

(86) PCT No.: PCT/GB2013/051165
§ 371 (c)(1),
(2) Date: Nov. 4, 2014

(87) PCT Pub. No.: WO2013/164642
PCT Pub. Date: Nov. 7, 2013

(65) Prior Publication Data
US 2015/0077747 A1   Mar. 19, 2015

(30) Foreign Application Priority Data

May 4, 2012   (GB) .................................. 1207881.2

(51) Int. Cl.
*G01N 21/00* (2006.01)
*G01N 21/31* (2006.01)
(Continued)

(52) U.S. Cl.
CPC ........... *G01N 21/31* (2013.01); *G01N 21/031* (2013.01); *G01N 21/64* (2013.01); *G01N 21/65* (2013.01);
(Continued)

(58) Field of Classification Search
CPC ...... G01N 21/31; G01N 21/031; G01N 21/64; G01N 21/65; G01N 21/4133;
(Continued)

(56) References Cited

U.S. PATENT DOCUMENTS 3,777,280 A * 12/1973 Pohl .................... H01S 3/08045
372/101
4,272,248 A *  6/1981 Neti ........................ G01N 21/64
250/461.1
(Continued)

FOREIGN PATENT DOCUMENTS

EP   1126256 A2   8/2001
EP   1146325 A2   10/2001
(Continued)

OTHER PUBLICATIONS

M. Trupke, E. A. Hinds, S. Eriksson, E. A. Curtis, Z. Moktadir, E. Kukharenka, and M. Kraft, Appl Phys Lett 89, 211106 (2005).
(Continued)

*Primary Examiner* — Hina F Ayub
(74) *Attorney, Agent, or Firm* — Harness, Dickey & Pierce, P.L.C.

(57) ABSTRACT

A sensor comprises a pair of mirrors (11, 12) opposed along an optical axis and shaped to provide an optical cavity with stable resonance in at least one mode and having a cavity length of at most 50 μm. An actuator system is arranged to move the mirrors relative to each other along the length of the optical cavity for tuning the wavelength of the mode of said cavity. A chemical sample is introduced inside the optical cavity using a sample introduction system (21). An EM radiation source (20) illuminates the cavity and a detector (25) detects the EM radiation emitted from, transmitted through, or reflected from the optical cavity.

30 Claims, 4 Drawing Sheets

(51) Int. Cl.
*G01N 21/03* (2006.01)
*G01N 21/64* (2006.01)
*G01N 21/65* (2006.01)
*G01N 21/41* (2006.01)

(52) U.S. Cl.
CPC . *G01N 21/4133* (2013.01); *G01N 2021/0346* (2013.01); *G01N 2021/651* (2013.01); *G01N 2201/06113* (2013.01)

(58) Field of Classification Search
CPC ..... G01N 2021/0346; G01N 2021/651; G01N 2021/06113
USPC .......................................................... 356/72
See application file for complete search history.

(56) References Cited

U.S. PATENT DOCUMENTS

| | | | |
|---|---|---|---|
| 4,556,979 A | 12/1985 | Scott et al. | |
| 4,751,712 A | 6/1988 | Pax et al. | |
| 5,298,965 A * | 3/1994 | Spirit | G01M 11/319 356/73.1 |
| 5,767,541 A * | 6/1998 | Hanagasaki | H01L 27/10805 257/295 |
| 5,871,698 A * | 2/1999 | Laguna | G01N 21/05 422/257 |
| 5,909,280 A | 6/1999 | Zavracky | |
| 6,795,190 B1 * | 9/2004 | Paul | G01J 3/42 356/437 |
| 6,839,140 B1 | 1/2005 | O'Keefe et al. | |
| 7,511,808 B2 | 3/2009 | Tong et al. | |
| 8,599,373 B1 * | 12/2013 | Djeu | G01J 3/44 356/300 |
| 8,976,834 B2 * | 3/2015 | Kaster | 372/92 |
| 2002/0168136 A1 | 11/2002 | Atia et al. | |
| 2002/0196548 A1 * | 12/2002 | Kuznetsov | H01S 5/18388 359/578 |
| 2005/0134836 A1 | 6/2005 | Paldus et al. | |
| 2005/0199820 A1 * | 9/2005 | Eastham | B82Y 10/00 250/396 R |
| 2006/0056463 A1 * | 3/2006 | Wang | G01J 3/10 372/3 |
| 2006/0268260 A1 | 11/2006 | Liu et al. | |
| 2007/0014505 A1 | 1/2007 | Hosomi et al. | |
| 2007/0252983 A1 | 11/2007 | Tong et al. | |
| 2008/0064975 A1 * | 3/2008 | Hancock | A61B 5/083 600/532 |
| 2008/0111077 A1 | 5/2008 | Miller | |
| 2008/0186494 A1 * | 8/2008 | Kiesel | G01N 21/0303 356/440 |
| 2009/0029402 A1 * | 1/2009 | Papkovsky | G01N 21/0332 435/29 |
| 2009/0059234 A1 | 3/2009 | Dreyer et al. | |
| 2009/0153844 A1 | 6/2009 | Peter et al. | |
| 2010/0045993 A1 * | 2/2010 | Martini | A61B 5/14532 356/436 |
| 2012/0013905 A1 | 1/2012 | Nozawa | |
| 2012/0128014 A1 * | 5/2012 | Gu | H01S 3/0627 372/22 |
| 2012/0200851 A1 * | 8/2012 | Wu | G01N 21/658 356/301 |
| 2014/0071446 A1 * | 3/2014 | Djeu | G01J 3/36 356/301 |
| 2015/0276590 A1 * | 10/2015 | Koulikov | G01N 21/1702 356/72 |

FOREIGN PATENT DOCUMENTS

| | | |
|---|---|---|
| EP | 1558955 A2 | 8/2005 |
| EP | 2444791 A1 | 4/2012 |
| GB | 2445956 A | 7/2008 |
| WO | WO-199934484 A2 | 7/1999 |
| WO | WO-2001/67171 A2 | 9/2001 |
| WO | WO-2004036700 A2 | 4/2004 |
| WO | WO-2004/083820 A2 | 9/2004 |
| WO | WO-2007/001367 A2 | 1/2007 |
| WO | WO-2011/0049582 A1 | 4/2011 |

OTHER PUBLICATIONS

M. Trupke, J. Goldwin, B. Darquie, G. Dutier, S. Eriksson, J. Ashmore, and E. A. Hinds, Phys Rev Lett 99, 063601 (2007).
T. Steinmetz, Y. Colombe, D. Hunger, T. W. Hansch, A. Balocchi, R. J. Warburton, and J. Reichel, Appl Phys Lett 89, 111110 (2006).
G. Cui, J. M. Hannigan, R. Loeckenhoff, F. M. Matinaga, M. G. Raymer, S. Bhongale, M. Holland, S. Mosor, S. Chatterjee, H. M. Gibbs, and G. Khitrova, Optics Express 14, 2291 (2006).
D. Hunger et al., A Fiber FabryPerot cavity with high finesse, New Journal of Physics vol. 12, 065038, 2010.
Dolan et al., "Femtoliter tunable optical cavity arrays", Optics Letters, vol. 35, No. 21, Nov. 2010.
G. Berden, R. Peeters and G. Meijer, Int. Rev. Phys. Chem., 19(4) 565 (2000).
J. J. Scherer, J. B. Paul, A. O'Keefeand R. J. Saykally, Chem. Rev., 97(1) 25 (1997).
M. D. Wheeler, S. M. Newman, A. J. Orr-Ewing and M. N. R. Ashfold, J. Chem. Soc., Faraday Trans., 94(3) 337 (1998).
S. M. Ball and R. L. Jones, Chem. Rev., 103(12) 5239 (2003).
D. B. Atkinson, Analyst, 128(2) 117 (2003).
S. S. Brown, Chem. Rev., 103 5219 (2003).
Chris Gell et al., Handbook of Single Molecule fluorescence spectroscopy (OUP, 2006), pp. 249-252.
Timothy Mcgarvey et al., Finesse and sensitivity gain in cavity-enhanced absorption spectroscopy of biomolecules in solution, Optics Express, 2006, vol. 14, Nr: 22, pp. 10441-10451.
K. Vahala Nature 424, p. 839 (2003).
Jarek Antoszewski et al., Towards MEMS based infrared tuneable micro-spectrometers, Proceedings of the SPIE 2002.
B. Helbo, S. Kragh, B. G. Kjeldsen, J. L. Reimers, and A. Kristensen, Sensors and Actuators A, 111 21 (2004).
Helbo et al., Micro cavity Fluidic Dye Laser, IEE 16th Annual Conf on MEMS 2003.
Trupke, M. et al., "Microfabricated high-finesse optical cavity with open access and small volume", Applied Physics Letters, 2005, vol. 87.
Cox A J & Scott G W, Piezoelectrically Tuned Short-Cavity Dye-Laser Design, Applied Optics, 1984, vol. 23, Nr: 8, pp. 1135-1137.
Notification of Transmittal of the International Search Report and the Written Opinion of the International Searching Authority, and International Search Report dated Aug. 1, 2013 for PCT Application No. PCT/GB2013/051165, filed May 3, 2013.

* cited by examiner

ACTIVE CHEMICAL SENSING USING OPTICAL MICROCAVITY

CROSS REFERENCE TO RELATED APPLICATIONS

This application is a U.S. National Phase Application under 35 U.S.C. 371 of International Application No. PCT/GB2013/051165 filed on May 3, 2013, which claims priority to British Patent Application No. 1207881.2 filed on May 4, 2012. The contents of the above applications are incorporated herein by reference.

The present invention relates to sensing of a chemical sample in an optical cavity, including without limitation sensing using cavity-enhanced spectroscopy techniques.

A number of techniques are known for performing sensing of a chemical sample using an optical cavity, including cavity ringdown and cavity-enhanced absorption spectroscopy, both of which can also be used to make sensitive measurements of any changes in refractive index of the medium within the cavity. Microscopic and nanoscopic optical cavities of dimensions less than around 10 μm bring particular advantages to these techniques, including sensitivity to minute absolute quantities of analyte. Such small cavities also enable new detection techniques such as cavity-enhanced fluorescence and cavity-enhanced Raman spectroscopy, as a result of an enhanced interaction strength between the electromagnetic field and the electronic system.

In a typical apparatus for performing cavity-enhanced absorption spectroscopy, the cavity is very large relative to the wavelength of the excitation light, and the mode spacing is correspondingly small. The bandwidth of a laser used to excite the cavity is generally broad enough that many longitudinal modes are excited and form stable resonances within the cavity. The modes can then undergo constructive and destructive interference, affecting signal quality. To achieve the best results in cavity ringdown measurements it is often necessary to employ narrowband lasers and sophisticated electronics to 'lock' the cavity to a single cavity mode, and to track the length of the cavity to follow the mode as the wavelength is scanned. Synchronising the laser scanning and cavity scanning electronics in such applications is crucial, and can be complex.

Similar issues exist in other types of sensing using an optical cavity.

According to the present invention, there is provided a method of sensing a chemical sample, the method comprising:

providing a pair of mirrors opposed along an optical axis and shaped to provide an optical cavity with stable resonance in at least one mode and having a cavity length of at most 50 μm;

further providing an actuator system arranged to move the mirrors relative to each other along the length of the optical cavity for tuning the wavelength of the mode of said cavity;

introducing a chemical sample inside the optical cavity;

illuminating the cavity with EM radiation capable of interacting with the chemical sample detecting the EM radiation emitted the optical cavity.

The present invention performs sensing using a micrometer scale optical microcavity. The use of the microcavity not only reduces the mode volume, but increases the Free Spectral Range (FSR), thereby facilitating filtering by a single mode of the optical cavity.

Accordingly, this form of optical filter offers a relatively narrow transmission band. This allows a relatively broadband light source to be employed, with the wavelength selection being employed by the cavity itself. Furthermore, this optical cavity may be implemented with a simple, inexpensive arrangement.

Furthermore, the actuator system provides tuning of mode and hence control of the excitation wavelength over a wide wavelength range, but with no requirement for tuning or frequency locking of an external light source. The actuation system may be any system that is capable of moving the mirrors relative to each other, for example a piezoelectric actuator. This offers major opportunities in reducing the cost and size of sensors.

The technique may be applied to a range of different types of sensing, including sensing that employs cavity-enhanced absorption spectroscopy, but also including sensing that exploits the sensitivity of the optical cavity to the refractive index of the medium therewithin.

The optical cavities may advantageously be designed to improve their spectral characteristics.

A number of configurations of the mirrors may be used to provide the optical cavity with a stable resonance for modes confined perpendicular to the optical axis between the mirrors. To provide such confinement, typically, at least one of the mirrors is concave. Stable resonant modes produced in this way are robust to misalignment of the two mirrors and to the angle of incidence of illuminating radiation.

The cavity length may be reduced, for example to be at most 30 μm, preferably at most 10 μm to increase the FSR which increases their tuning range and increases the spectral separation of the modes confined perpendicular to the optical axis which aids in producing single mode transmission, and also reduces the mode volume. This allows the sensor to be designed to provide good mode control, good field of view (low sensitivity to the angle of angle of incidence of illuminating radiation), and a useful quantum mechanical enhancement of coupling between the optical and electronic systems.

Minimisation of the radius of curvature increases the spectral separation of the modes confined perpendicular to the optical axis which aids in producing single mode transmission, and also reduces the mode volume. In that case, the concave mirror preferably has a relatively low radius of curvature, for example at most 50 μm, preferably at most 30 μm or 10 μm or 3 μm.

Advantageously, one of the mirrors is concave and the other one of the mirrors is planar. This avoids the need to provide alignment of the mirrors perpendicular to the optical axis between the mirrors.

Concave mirrors of small size may be formed by focussed ion beam milling.

Advantageously, the reflectivity of the mirrors is maximised in order to maximise the quality factor Q. This minimises the width of the modes and thereby provides increased sensitivity. Advantageously, the mirrors have a root-mean-square roughness of at most 1 nm, and/or a reflectance of at least 99%, preferably at least 99.5%. Advantageously to provide high reflectivity, the mirrors may be Bragg reflectors.

According to a further aspect of the present invention, there is provided a sensor for performing chemical sensing arranged to implement a similar method.

To allow better understanding, an embodiment of the present invention will now be described by way of non-limitative example with reference to the accompanying drawings, in which.

Figure 3A:
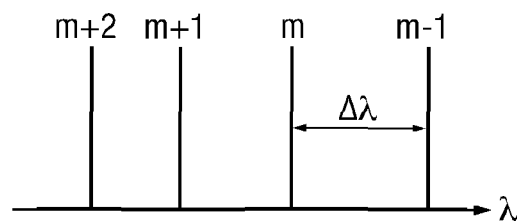
Figure 3B:
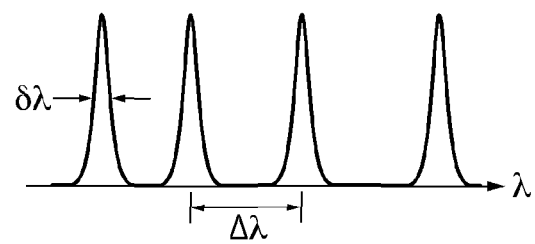
Figure 4:
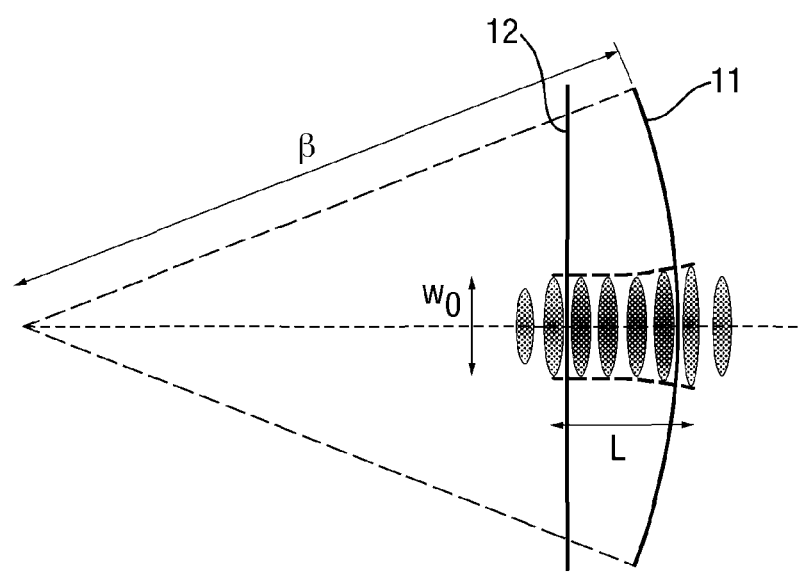
Figure 5:
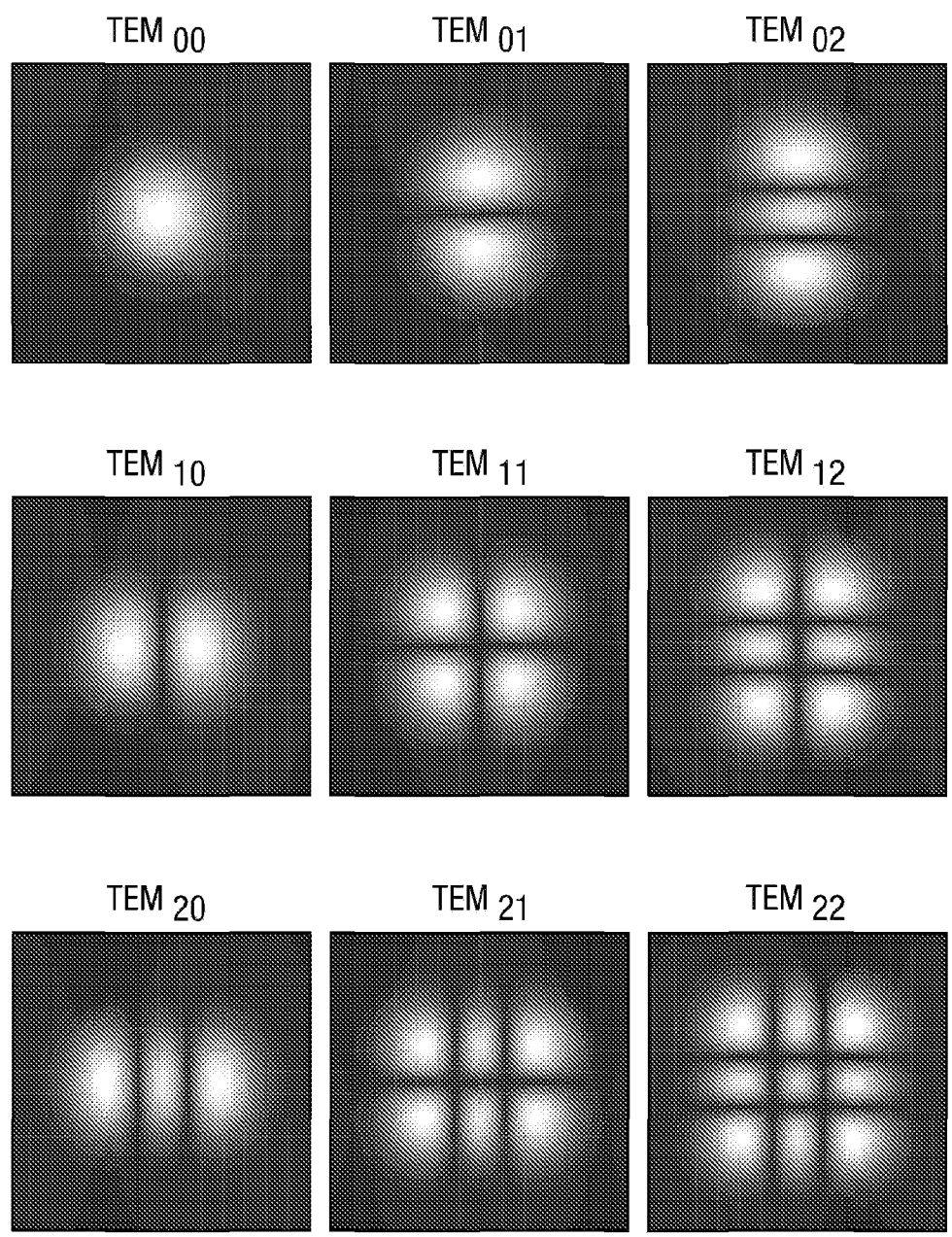
Figure 6A:
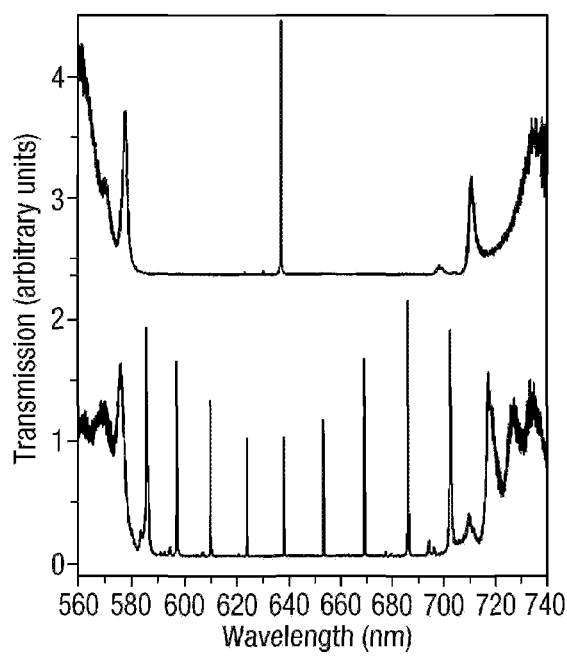
Figure 6B:
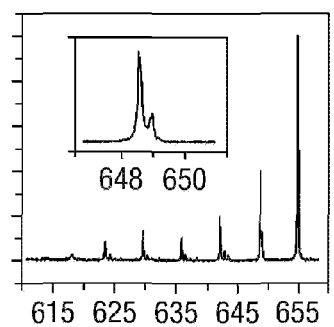
Figure 6C:
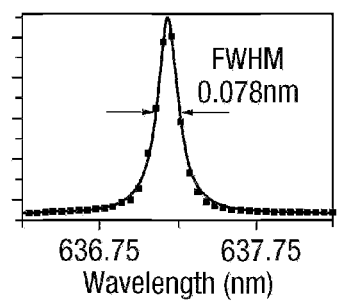

FIGS. 3(a) and 3(b) are plots of an intensity spectrum of an optical cavity with no losses and losses, respectively, illustrating the mode structure;

FIG. 4 is a side view of the optical cavity illustrating dimensional quantities;

FIG. 5 is a set of plots of spatial distributions of the first nine Hermite-Gauss $TEM_{mn}$ cavity modes perpendicular to the optical axis;

FIGS. 6(a) to (c) are measured transmission spectra of an optical cavity; and

Figure 7:
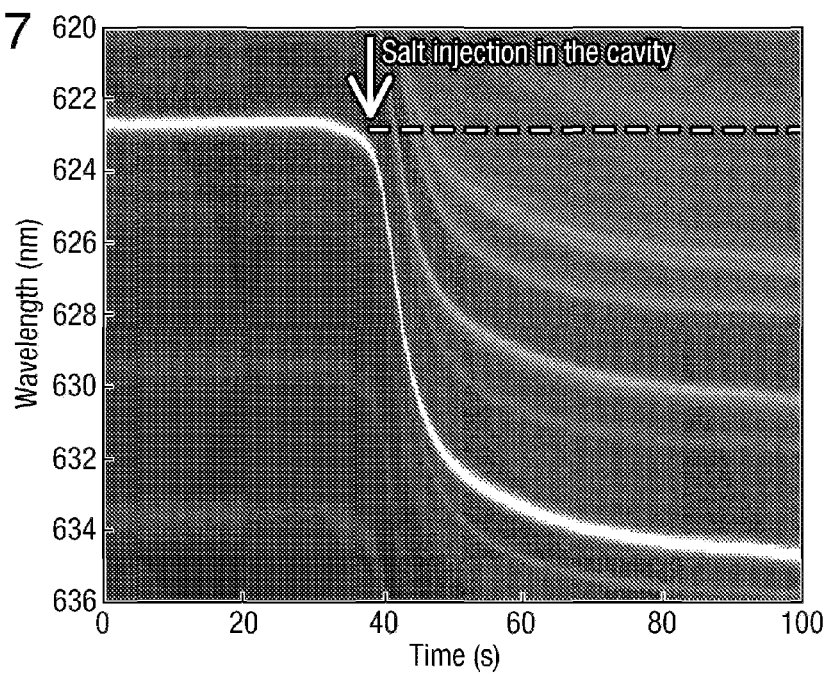

FIG. 7 is a colour-scale plot of the spectrum of light transmitted through an optical cavity as a function of time in an experimental example.

The present invention is applied generally to EM radiation including in any combination: ultraviolet light (which may be defined herein as having wavelengths in the range from 10 nm to 380 nm); visible light (which may be defined herein as having wavelengths in the range from 380 nm to 740 nm); infrared light (which may be defined herein as having wavelengths in the range from 740 nm to 300 µm); and/or other wavelengths. Herein, the terms 'optical' and 'optics' are used to refer generally to the EM radiation to which the invention is applied.

Figure 1:
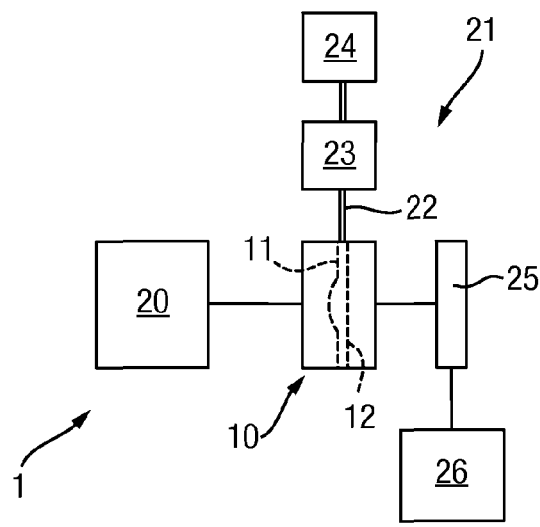
FIG. 1 is a diagram of a sensor.
Figure 2:
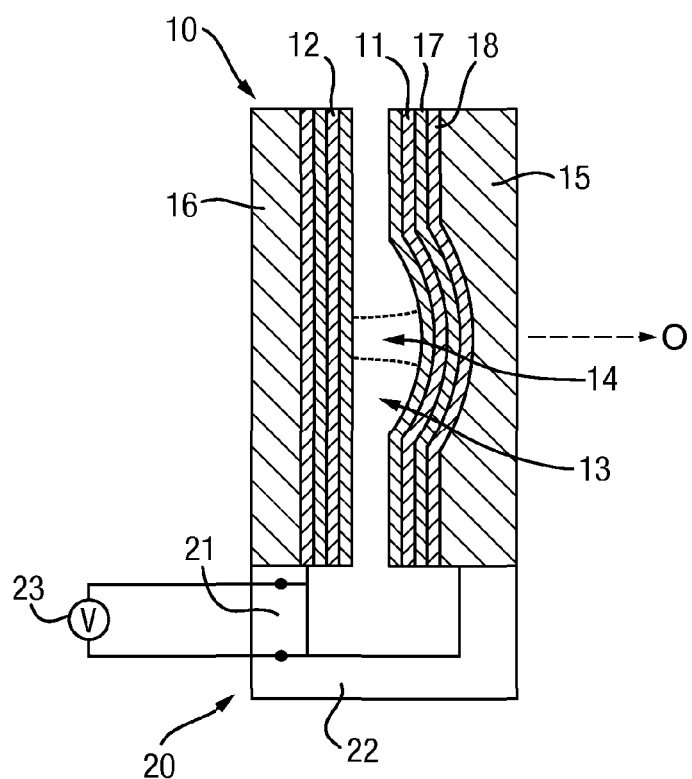
FIG. 2 is a side view of a cavity arrangement.

A sensor 1 that is arranged to perform a miniature tunable dye laser is shown in FIG. 1. The sensor 1 comprises a cavity arrangement 10 shown in detail in FIG. 2 and arranged as follows.

The cavity arrangement 10 is an open-access optical microcavity that comprises a pair of mirrors 11 and 12 opposing each other along the optical axis O. The microcavity is referred to as 'open access' because the mirrors 11 and 12 are open at the sides, transverse to the optical axis, thereby providing open access to the space therebetween.

The space between the mirrors 11 and 12 may be free space (vacuum), gas (e.g. air or other gas) or liquid.

The mirrors 11 and 12 are formed on substrates 15 and 16 and are shaped to provide an optical cavity 13 therebetween. An optical cavity confines EM radiation, such that the electromagnetic field has a stable resonance and forms standing waves of discrete frequencies and spatial distributions. Each standing wave state is known as a 'mode' of the EM field. For each mode, constructive interference of the electromagnetic waves occurs when a single 'round trip' of the cavity is described. The mirrors 11 and 12 are shaped so that the optical cavity 13 has stable resonance for at least one mode 14 that is confined in three dimensions, that is along and perpendicular to the optical axis O by reflection at the mirrors 11 and 12, as shown schematically in FIG. 2 (and also FIG. 4).

The cavity length L of the optical cavity 13 is the distance between the mirrors 11 and 12 including the field penetration into the mirrors 11 and 12.

There will now be given a general description of optical cavities that applies to the optical cavity 13.

By way of illustration for the confinement in the dimension along the optical axis O between the mirrors 11 and 12, the modes occur at wavelengths where the cavity length L (optical length of the cavity 13) is an integer number of half-wavelengths of the EM radiation, so that a round trip corresponds to an integer number of whole wavelengths. The criterion for a stable mode to exist in a planar Fabry Perot cavity may be written as $$m\lambda = 2L \quad (1)$$

where m is an integer, $\lambda$ is the optical wavelength inside the cavity and L is the cavity length. The mode wavelengths therefore form a series of discrete values corresponding to different values of m, as shown in FIG. 3(a) for the idealised cavity with no losses and in FIG. 3(b) for a real cavity with losses. In frequency space, the resulting cavity spectrum is often referred to as a 'frequency comb'. For a given cavity, the lower limit of m may be 1, or the range of m values may be determined by the range of wavelength for which the mirrors 11 and 12 are reflective.

The Free Spectral Range (FSR) is the separation of the modes in wavelength space. For the illustrative one-dimensional example, the FSR is derived from equation 1 as $$\Delta\lambda = \frac{\lambda^2}{2L} \quad (2)$$

Thus, the FSR can be seen to increase as the cavity length L is reduced. In general optical cavities with small cavity length L therefore contain fewer modes, spaced further apart in wavelength than the modes in optical cavities with large L.

The above text refers to a simple one-dimensional example, but the same principles apply for confinement in three dimensions in the optical cavity 13.

Equation 1 appears to imply that each individual mode (i.e. each value of m) has an exactly defined wavelength as shown in FIG. 3(a), but this simple picture is modified by leakage of EM radiation from the cavities, which results in each mode having a finite width $\delta\lambda$ as shown in FIG. 3(b). This width $\delta\lambda$ is related to the rate $\eta$ at which photons leak from the cavity by the expression $$\delta\lambda = \frac{\eta\lambda^2}{2\pi c} \quad (3)$$

where c is the speed of light in the cavity. The quality factor Q of a mode is defined as the ratio of the absolute resonant wavelength (the peak wavelength of the mode) and the mode width, that is $$Q = \frac{\lambda}{\delta\lambda} = \frac{\omega}{\delta\omega} \quad (4)$$

where $\omega$ is the angular frequency of the EM radiation in the cavity mode and $\delta\omega$ is the mode width in angular frequency space. The quality factor Q is equivalent to the average number of optical cycles a photon undergoes within the cavity before it escapes. The quality factor may be attributed to the cavity itself, in which case it refers to the highest Q modes that the optical cavity supports.

Another important parameter for an optical cavity is the 'mode volume', which we label V. This represents the physical volume that is occupied by the majority of the energy in the optical mode. The energy density of an electromagnetic field is given by the product of the dielectric permittivity $\epsilon$ and the electric field intensity $|E|^2$. The mathematical definition of the mode volume is then the ratio of the total mode energy to the peak energy density, given by the equation:

$$V = \frac{\iiint_{all\ space} \epsilon(\vec{r})|E(\vec{r})|^2 dV}{(\epsilon|E|^2)_{max}} \quad (5)$$

Conversely, if the mode volume is known, then the maximum root-mean-square (rms) electric field can be calculated for a specified number N of photons present, based on the total energy of a mode containing this number of photons $$\xi = \sqrt{\frac{\left(N+\frac{1}{2}\right)\hbar\omega}{\varepsilon V}} \qquad (6)$$

In general terms, the smallest resonant cavity that can be achieved theoretically is a cube of side length $\lambda/2$ with perfectly reflecting walls (no field penetration), giving a mode volume of $$V = \frac{\lambda^2}{8}.$$

Many applications of optical cavities involve the interaction between the cavity field and electronic transitions of matter within the cavity. Electrons couple most strongly to electromagnetic radiation through the electric dipole interaction, whereby an electric dipole (a spatial separation of positive and negative charge) experiences a force due to the oscillating local electric field, whereby it can undergo a transition to a different state. For a transition dipole moment $\mu$ oriented parallel to the cavity field $\xi$, and energetically resonant with the optical mode, the strength of this coupling is characterised by the rate of energy transfer between the dipole and the field, known as the coherent coupling rate g $$g = \frac{\mu\xi}{\hbar} = \sqrt{\frac{\left(N+\frac{1}{2}\right)\mu^2\omega}{\hbar\varepsilon V}} \qquad (7)$$

Qualitatively different behaviour occurs in the limits where (i) EM radiation leaks out of the cavity before it can be reabsorbed by the dipole (g<<η), and (ii) energy can transfer back and forth between the dipole and field before leaking from the cavity (g >> η). These are known as the 'weak coupling' and 'strong coupling' limits respectively. The criterion for strong coupling is therefore $$\frac{Q}{\sqrt{V}} \gg \sqrt{\frac{\hbar\omega\varepsilon}{\mu^2\left(N+\frac{1}{2}\right)}}. \qquad (8)$$

The stringent requirement on cavity leakage makes strong coupling difficult to achieve.

In the weak coupling limit, the spontaneous emission rate of a resonant dipole is modified from the free-space value $$\gamma = \frac{\mu^2\omega^2}{3\pi\varepsilon\hbar c^2} \qquad (9)$$

to a new value $$\gamma' = \frac{g^2(v=0)}{2\kappa} = \frac{\mu^2 Q}{4\hbar\varepsilon V} \qquad (10)$$

that corresponds to an enhancement factor, known as the Purcell factor, $$F_P = \frac{\gamma'}{\gamma} = \frac{3\lambda^2 Q}{4\pi^2 V} \qquad (11)$$

This demonstrates that a cavity can modify the optical emission behaviour of a particle, of significance for applications in fluorescence detection and lasing. Importantly, equations 8 and 11 reveal that for strong coupling, or for modified spontaneous emission, large Q and small mode volume V are required.

The design parameters and general properties of the specific optical cavity 13 will now be described. In the following section there are described fabrication methods we use that allow us to combine mode volumes of order $\lambda^3$ with values of the quality factor Q in excess of $10^4$.

In this example, three dimensional optical confinement is achieved by one mirror 11 being concave. The concave shape of the mirror 11 is spherical, but this is not essential and the mirror 12 could alternatively have another rotationally symmetric shape or a non-symmetric shape. The other mirror 12 is planar. An optical cavity 13 in which stable modes are formed is provided by a radius of curvature β of the concave mirror 11 being greater than the length L of the optical cavity 13, as illustrated in FIG. 4, as shown in FIG. 4.

As a result of the concave shape of the mirror 11, In addition to the longitudinal optical mode structure described above, the optical cavity 13 possess transverse electromagnetic modes with Hermite-Gauss mode structure as shown in FIG. 5. Each longitudinal mode has a fundamental transverse mode ($TEM_{00}$) and a family of transverse harmonics $TEM_{mn}$ (integers m+n>0) at regular intervals on its short wavelength side. Some simple analytic equations can be used to describe this mode structure in the limit that β is significantly larger than L (known as the paraxial approximation).

The wavelength separation of the TEM modes with incrementing (m+n) is given by $$\Delta\lambda_T = \frac{\lambda^2}{2\pi L}\cos^{-1}\left(\sqrt{1-\frac{L}{\beta}}\right) \qquad (12)$$

revealing that the mode separation increases as the radius of curvature decreases and as the cavity length decreases. For the $TEM_{00}$ modes the cross sectional intensity distribution is Gaussian in shape, and the beam waist is situated on the planar mirror.

The waist width $w_0$ (the minimum width of the optical mode being the width at the planar mirror 12) is given by $$w_0^2 = \frac{\lambda L}{\pi}\sqrt{\left(\frac{\beta}{L}-1\right)} \qquad (13)$$

whereby the mode volume is given by $$V = \frac{\pi w_0^2 L}{4} \quad (14)$$

Therefore, for example, a radius of curvature β=2λ combined with a cavity length L=λ would lead to a mode volume $$V = \frac{\lambda^2}{4}.$$

The optical cavity has a cavity length of at most 50 μm, preferably at most 30 μm, more preferably at most 10 μm. Use of a microcavity with such a relatively short cavity length L increases the FSR, and also reduces the mode volume.

The concave mirror 11 has a radius of curvature of at most 50 μm, preferably at most 30 μm, more preferably at most 10 μm. Use of a microcavity with such a relatively short radius of curvature β increases the separation $\Delta\lambda_T$ of the $TEM_{mn}$ modes and may result in improved single mode transmission of EM radiation.

The mirrors 11 and 12 are formed to provide high reflectivity in order to maximise the quality factor Q. This minimises the width of the modes and thereby provides increased spectral resolution. Advantageously, the mirrors 11 and 12 have a reflectance of at least 99%, preferably at least 99.5%. To minimise losses, advantageously, the mirrors 11 and 12 have a root-mean-square roughness of at most 1 nm, and/or.

In particular the mirrors 11 and 12 may be Bragg reflectors. Such Bragg reflectors may comprise with multiple pairs of layers 17 and 18 alternating high and low refractive index dielectric material such as $TiO_2/SiO_2$, $ZrO_2/SiO_2$, $Ta_2O_5/SiO_2$, or $ZnS/Al_2O_3$. Each layer 17 and 18 is $\lambda_c/4n$ in thickness, where $\lambda_c$ the selected 'centre wavelength' for highest reflectivity and n is the refractive index of the layer. These combinations provide high index contrast resulting in small field penetration depths into the mirror, and low optical absorption at most optical wavelengths. A chosen mirror design (materials used, number of pairs) will determine the maximum reflectivity and the range of wavelengths (the band width) over which the mirrors are effective. This band width can typically be of order 100 nm for a mirror operating in the visible region of the spectrum.

As an alternative in some applications, the mirrors 11 and 12 may be metal mirrors, although these tend to absorb a few per cent of incident EM radiation at optical wavelengths and so are not suitable for the highest Q factor cavities.

A further limiting factor to the achievable reflectivity is scattering due to roughness of the coated surfaces. With a root-mean-square roughness σ the maximum reflectivity that can be achieved is $$R_{max} = e^{-\left(\frac{4\pi\sigma}{\lambda}\right)^2}. \quad (13)$$

For high reflectivities it is therefore desirable to be able to fabricate the concave surface with minimal roughness. Advantageously, the mirrors 11 and 12 have a root-mean-square roughness of at most 1 nm.

Other losses can be experienced due to edge effects if the concave mirror deviates from the ideal shape within the spatial extent of the mode.

The mirrors 11 and 12 have a reflectance of at least 99%, preferably at least 99.5%, but the reflectivity of such Bragg reflectors on substrates 15 and 16 of suitable material can reach 99.9999%, whereupon it generally becomes limited by trace absorption in the dielectric materials. Use of such relatively high reflectivities increase the quality factor Q.

In view of the above construction, the optical cavity 13 may be provided with a configuration providing small mode volumes and high quality factors Q. Therefore it is possible to provide the optical cavity with effectively a single mode within a wavelength band of interest.

The mirror 11 may be manufactured as follows.

The mirror 11 may be made using an etching technique to produce concave surfaces in silicon and thereby to fabricate cavities for single atom detection as disclosed in References [1] and [2] (that are incorporated herein by reference) (the References being cited at the end this description).

The mirror 11 may be formed by depositing mirrors onto convex surfaces such as silicon microlenses and then transfer them onto fibre tips using a lift-off technique as disclosed in Reference [3] (that is incorporated herein by reference).

The mirror 11 may be formed by using a bubble trapping method in glass to produce highly spherical surfaces with radii of curvature of order 50 μm, as disclosed in Reference [4] (that is incorporated herein by reference).

The mirror 11 may be formed by optical ablation of silica using a $CO_2$ laser, which has been demonstrated to be capable of providing Q factors of order $10^6$, and mode volumes as small as 2 μm$^3$, as disclosed in Reference [5] (that is incorporated herein by reference).

The preferred method to form the mirror 11 is to use focussed ion beam milling. For example, it is possible to apply the technique disclosed in Reference [6] (that is incorporated herein by reference). In this example, a gallium beam of current 5 nA and acceleration voltage 30 kV is rastered over a planar substrate, modulating the dwell time between 0.1 ms and 50 ms at each point to produce the desired features. The advantage of this method is that control over the shape of the concave surface is achievable at the nanometre length scale, whilst retaining sub nanometre roughness. In this way concave features of any desired radius of curvature down to about 100 nm, or possibly less, can be achieved, and coated with high reflectivity mirrors. It should be noted that mirrors in the form of high reflectivity Bragg reflectors are typically a few micrometres thick, which may place a limitation on the minimum size of concave feature that would be preserved after coating. Nevertheless significant reductions in mode volume are possible using this technique, as compared to the other techniques mentioned above.

So far using this technique, the inventors have achieved mode volumes as small as 0.5 μm$^3$, corresponding to ~6λ$^3$, at an operating wavelength of 440 nm in a 1.44 refractive index fluid, using a cavity with β=7 μm and L=1.6 μm. This mode volume has combined with a Q factor of 1000, and Q factors of up to 18,000 have been achieved using larger cavities.

The optical cavity 13 formed by a convex mirror 11 and a planar mirror 12 is advantageous in that the use of the planar mirror 12 avoids the need to provide alignment of the mirrors 11 and 12 perpendicular to the optical axis O between the mirrors 11 and 12. However, the mirrors 11 and 12 may have alternative shapes to provide an optical cavity. In general terms, the mirrors may each be curved with respective radii of curvature β and γ (where a planar mirror has an infinite radius of curvature, provided that in order to provide stable resonances, the mirrors 11 and 12 meet the requirement that $0 \leq (1-(L/\beta))\cdot(1-(L/\gamma)) \leq 1$. Further details of alternative forms of the optical cavity 13 are given in Reference [7] (that is incorporated herein by reference).

To provide tuning of the wavelength of the modes of the optical cavity 30, the apparatus 1 is further provided with an actuator system 20 that is arranged to move the mirrors 11 and 12 relative to each other along the length of the optical cavity 13 between the mirrors 11 and 12. In particular, the actuator system 20 comprises a piezoelectric actuator 21 that is arranged between the mirrors 11 and 12 with extension parallel to the optical axis O. One of the mirrors 11 is mounted directly on a support 22 and the other mirror 12 is mounted on the support 22 by the piezoelectric actuator 21, although other constructions for mounting the piezoelectric actuator 21 between the mirrors 11 and 12 are possible. The piezoelectric actuator 21 is driven by a drive signal supplied from a drive circuit 23 to provide positional control.

The mode structure of the optical cavity 13 can be characterised by measuring the optical transmission spectrum for broad band incident EM radiation. By way of example, FIG. 6 shows some typical transmission spectra derived from an optical cavity 13 made by the technique disclosed in Reference [6], illustrating the tunability, quality factor, and Hermite Gauss mode structure. FIG. 6(*a*) shows the transmission spectra for two cavities each with β=7 μm at L=3.0 μm and L=12.3 μm, respectively. This shows how the FSR increases as L is reduced. FIG. 6(*b*) is a close-up of the Hermite-Gauss mode structure from a single longitudinal mode. $TEM_{00}$ is at 655 nm, $TEM_{01}$ and $TEM_{10}$ are at 649 nm, etc. FIG. 6(*b*) shows a splitting observed between with $TEM_{01}$ and $TEM_{10}$ resulting from a slight deviation from cylindrical symmetry. FIG. 6(*c*) shows a high Q longitudinal resonance (scatter) with Lorentzian curve fit (solid line). The resolution of the spectrograph used for the measurements is about 0.05 nm, contributing substantially to the line width observed.

An EM radiation source 20 is arranged to illuminate the optical cavity 13 of the cavity arrangement 10 with EM radiation having a band of wavelengths. The EM radiation source 20 and cavity arrangement 10 are selected so that the optical cavity 13 has at least one mode, preferably a single mode, which is more preferably a $TEM_{00}$ mode, at a wavelength within the band of wavelengths of the EM radiation source 20. The EM radiation source 20 is selected so that the EM radiation is capable of interacting with the sample of interest.

The sensor 1 comprises a sample introduction system 21 that is arranged to introduce a chemical sample inside the optical cavity 13. This is straightforward due to the mirrors 11 and 12 providing open access to the space therebetween. The sample introduction system 21 may comprise a container 24 containing the sample, channels 22 providing a flow path from the container 24 into the optical cavity 13 between the mirrors 11 and 12 through and a pump 23 for pumping the sample through the channels 22. The sample may be is a gas or liquid sample.

The sensor 1 comprises a detector 25 arranged to detect the EM radiation emitted from the optical cavity 13 through one of the mirrors 11 or 12. The detector 25 may be any suitable type of detector, for example a CMOS (complimentary metal-oxide-semiconductor) or CCD (charge-coupled device) detector, photodiode, or photomultiplier.

In this example, the EM radiation source 20 illuminates the optical cavity 13 along the axis of the cavity between the two mirrors 11 and 12 and the detector 24 detects the EM radiation emitted from the optical cavity 13 along the cavity axis through one of the mirrors 11 or 12, i.e. the EM radiation transmitted through the optical cavity 23. More generally, other configurations of the EM radiation source 20 and detector 23 are possible, including configurations where the EM radiation source 20 and/or detector 23 are disposed laterally of the cavity axis, and/or including configurations where the emitted EM radiation detected by the detector 25, is EM radiation that is transmitted through the optical cavity 13, reflected by the optical cavity 13, or emitted by the sample itself, e.g. by fluorescence.

Lastly, the sensor 1 comprises an analysis unit 26 that receives the detection signal output by the detector 25 and analyses it to provide a signal indicating the result of the sensing. The analysis unit 26 may be implemented by a computer apparatus executing an appropriate program, for example a conventional personal computer. Alternatively, the analysis unit 26 may be implemented in part or full by dedicated hardware, for example a field programmable gate array (FPGA) or application-specific integrated circuit (ASIC).

The sensor 1 may be applied to range of different types of sensing, typically to sense an analyte in the sample. Some non-limitative examples of sensing to which the sensor 1 may be applied will now be described.

In one type of sensing exploiting absorption, the actuator system 20 is used to tune the wavelength of the mode of the optical cavity 13 to match an absorption wavelength of the analyte. In that case, the analysis unit 26 analyses the detected EM radiation to detect a reduction in the detected EM radiation at that wavelength, which is indicative of the presence of the analyte.

One example of such a technique employing sensing uses cavity-enhanced spectroscopy methods, for example cavity-enhanced absorption spectroscopy or cavity-based absorption spectroscopy.

Cavity-enhanced absorption spectroscopy techniques, for example as disclosed in Reference [7], employing macroscopic cavities (typically of length from around 0.1 to 1.0 m) are well-established for making ultrasensitive spectroscopic absorption measurements, primarily on gas phase samples. Absorption of light by molecules is usually described in terms of the Beer-Lambert law:

$$I = I_0 e^{-\alpha Cl} \qquad (1)$$

where I and $I_0$ are the intensities of the light transmitted through the sample and incident on the sample, respectively, α is the molecular absorption coefficient, C is the sample concentration, and l is the path length through the sample. For a known path length l, a measurement of I and $I_0$ allows the quantity κ=αC, the absorption per unit path length, to be determined. If the absorption coefficient α is known, this allows the concentration to be determined, and vice versa. From Equation (1), it is clear that the sensitivity of the measurement can be improved by increasing the optical path length, l. Cavity-based spectroscopies achieve this without increasing the physical size of the sample, by trapping light within an optical cavity such that it undergoes a large number of passes through the sample.

EM radiation from the EM radiation source 20 is coupled through one of the mirrors 11 and 12 and is confined within the optical cavity 13, undergoing repeated reflections back and forth between the mirrors 11 and 12. A small amount leaks out through the mirrors 11 and 12 on each reflection. The detector 25 therefore outputs a detection signal that is proportional to the light intensity remaining within the optical cavity 13. If the optical cavity 13 is excited with a pulse of light, the constant fraction of light leaking out on each round trip of the optical cavity 13 yields an intensity that decays exponentially with time, with the time constant, or 'ringdown time', t, depending only on the cavity geometry (cavity length L) and the cavity losses (primarily through imperfect mirror reflectivity).

$$t = \frac{L}{c(1-R)} \quad (2)$$

where c is the speed of light. The factor L/c is the time taken for one pass through the cavity, and the second factor $1/(1-R)$ quantifies the number of passes through the cavity. If an absorbing sample is placed within the cavity, the cavity losses are increased, leading to a reduction in the ringdown time.

$$t = \frac{L}{c(1-R+\kappa l)} \quad (3)$$

With κl being the 'Beer-Lambert law' absorbance of the sample (as per Equation (1)). In all examples covered here, the absorption path length l is equal to the cavity length L, but this does not have to be the case in general.

The analysis unit 26 is arranged to analyse the detection signal to measure the ringdown times $\tau$ and $\tau_0$ in the presence and absence of sample, respectively, allows the absolute absorption, $\kappa = \alpha C$, to be determined in accordance with the equation:

$$\kappa = \frac{L}{cl}\left(\frac{1}{t} - \frac{1}{t_0}\right) \quad (4)$$

The ringdown time is measured as the wavelength of the EM radiation is scanned, and so the analysis unit 26 generates an absorption spectrum of the sample. Further details of cavity ringdown spectroscopy which may be applied in the sensor 1 are disclosed in References [8] to [10] (which are incorporated herein by reference).

By integrating the ringdown signal over time, it is straightforward to show that the total detected light intensity is proportional to the ringdown time $\tau$. This realisation led to the development of an experimentally simpler alternative to cavity ringdown spectroscopy known as cavity enhanced absorption spectroscopy (CEAS), which may alternatively be employed in the sensor.

In CEAS, the EM radiation source excites the optical cavity 13 with a pulsed or continuous-wave beam, and analysis unit 26 measures the total intensity of EM radiation transmitted through the optical cavity 13 rather than the time-dependent ringdown signal. The analysis unit 26 determines the absorption κ at the excitation wavelength from a measurement of the signal S and $S_0$ (now taking the form of an intensity rather than a ringdown time) in the presence and absence of the sample of interest, respectively, in accordance with the equation:

$$\kappa l = \left(\frac{S_0}{S} - 1\right)(1-R) \quad (5)$$

The factor $1/(1-R)$, the inverse of which appears in equation (5), is known as the cavity enhancement factor, and quantifies the improvement in sensitivity relative to a single pass measurement. As in cavity ringdown spectroscopy, the absorption spectrum $\kappa(\lambda)$ may be obtained by scanning the laser wavelength λ and recording the signal intensity at each point.

In the existing cavity-enhanced spectroscopy methods outlined above, the cavity is very large relative to the wavelength of the excitation light, and the mode spacing is correspondingly small. The bandwidth of the laser used to excite the cavity is generally broad enough that many longitudinal modes are excited and form stable resonances within the cavity. The modes can then undergo constructive and destructive interference, affecting signal quality. To achieve the best results in cavity ringdown measurements it is often necessary to employ narrowband lasers and sophisticated electronics to 'lock' the cavity to a single cavity mode, and to track the length of the cavity to follow the mode as the wavelength is scanned. Synchronising the laser scanning and cavity scanning electronics in such applications is crucial, and can be complex.

In contrast, the sensor 1 offers an alternative approach employing an optical cavity of dimensions commensurate with the wavelength of the excitation EM radiation. The optical cavity 13 is so small, and the free spectral range so large, that a single cavity mode (excitation wavelength) can be preferentially excited with a broadband source. Furthermore, the resonant wavelength of the cavity may be tuned to any desired value simply by moving the mirrors using actuation system 20. As a consequence, the EM radiation source 20 may be a low-cost broadband light source, with no requirement for locking the frequency of the source to a cavity mode. Only the resonant wavelength will form a stable mode within the optical cavity 13, with all other wavelengths undergoing destructive interference.

For use in chemical sensing, the optical cavity 13 is tuned to the wavelength of a characteristic absorption line for the analyte of interest, and a drop in intensity of the cavity output will be observed when the analyte is present within the cavity, as quantified in Equation (5).

The sensor 1 may be used for sensing of both gas-phase and solution or liquid phase samples. Gas phase absorption spectra consist of sharp lines corresponding to transitions between individual rovibronic states of the molecule. It is generally possible to identify a rotational line that is sufficiently unique to the molecule of interest that it can be used to identify it unambiguously in a gaseous sample. The high Q factor of the microcavities ($Q=10^4$ has been demonstrated and $Q=10^5$-$10^6$ will be possible when higher reflectivity mirror coatings are employed) yields resonances that are sufficiently sharp that the cavity can be tuned to a single rotational line. For example, a Q factor of $10^4$ yields cavity modes with a bandwidth of the order of 0.1 nm, while a cavity with a Q factor of $10^6$ would have resonances of width of the order of 1 pm. The sensor 1 therefore offers a general platform for gas-phase chemical sensing.

In solution, molecular energy levels are broadened by interactions with the solvent, and individual rovibronic transitions tend to coalesce to form broad, relatively unstructured absorption bands. In some cases an analyte will have a strong absorption at a wavelength that is not shared by other molecules present, but more often than not there will be spectral interferences from other chemical species present in the sample. This problem may be addressed by using simple colourimetric reactions to convert the analyte of interest selectively into a strongly coloured derivative compound. By monitoring the absorption of the derivative, which is much stronger than that of any potential interferents, the initial concentration of the analyte of interest may be established. An example of such a conversion is the Griess reaction for the quantification of nitrite concentrations in liquid samples. The 'Griess reagent' converts free nitrite into a strongly absorbing azo dye, with a 1:1 correlation between the dye concentration and the initial concentration of nitrite.

The sensitivity of CEAS to the presence of an absorbing species may be considered in terms of Equation (5). We have previously defined the cavity enhancement factor, $1/(1-R)$, which is maximised by using mirror coatings that are as highly reflective as possible. Mirrors coatings of reflectivity R=0.9998 are widely available, and would yield a cavity enhancement factor of 5000, while the best mirror coatings currently on the market, with stated reflectivity of 0.999997, and would yield a cavity enhancement factor of over 300 000.

The detection sensitivity in a CEAS measurement is determined by the minimum change in the intensity of transmitted light that can be reliably quantified. This is often taken to be three times the standard deviation in a measurement of the baseline signal $S_0$. Taking as a conservative estimate that the sensor 1 could reliably detect a 1% change in signal intensity, a cavity 13 of cavity length 1 μm employing the best available mirrors would allow detection of a minimum absorption per unit pathlength of $\kappa_{min}=3\times 10^{-4}$ cm$^{-1}$. Translating this into a minimum detectable concentration of sample requires knowledge of the molecular absorption coefficient of the molecule of interest at the excitation wavelength of the cavity.

Absorption coefficients vary widely. For example, the azo dye product of the Griess reaction outlined in the previous section has an absorption coefficient of around $80\times 10^3$ M$^{-1}$ cm$^{-1}$ at 520 nm (molecular absorption cross section of $1.3\times 10^{-16}$ cm$^2$), and a detectable absorption per unit pathlength of $3\times 10^{-4}$ cm$^{-1}$ would correspond to a minimum detectable concentration of 3.75 nM. Considering that the mode volume of a cavity 13 of cavity length 1 μm with concave mirror 12 with a radius of curvature β of 10 μm is around $3\times 10^{-19}$ m$^3$, it is envisaged that the technique should be able to record the presence of a few molecules, and possibly even single molecules, within this volume. When using less highly reflective mirrors or less strongly absorbing target molecules, the detection sensitivities will be correspondingly reduced.

In another type of sensing, the sensor 1 employs the sensitivity of the optical cavity 13 to the refractive index of the medium therewithin. In this case the analysis unit 26 analyses detection signal to detect a change in the refractive index of the medium within the optical cavity that is indicative of an analyte.

Since the wavelength of EM radiation in a medium is given by $\lambda_0/n$, where $\lambda_0$ is the vacuum wavelength and n the refractive index of the medium, the optical cavity 13 may be used to monitor changes in refractive index with very high precision, on the order of 1/Q. There are two approaches.

In the first approach, the EM radiation source 20 is a broadband source and so a change in refractive index leads to a shift in the wavelength transmitted through the cavity. In this case, the detector 25 is a wavemeter or high resolution spectrometer that detects the wavelength of the incident EM radiation. The analysis unit 26 measures the refractive index within the cavity quantitatively from the detection signal representing the wavelength and detects a change in the refractive index that is indicative of an analyte.

In the second approach, the EM radiation source 20 is a narrowband laser and the cavity length is mode matched to the laser wavelength, so that a change in refractive index brings the cavity in or out of resonance with the excitation wavelength, manifesting as a change in intensity of the light transmitted through the cavity. In this case, the detector 25 simply detects the intensity of the incident EM radiation. The analysis unit 26 analyses the detection signal and detects a change in the refractive index that is indicative of an analyte. In this setup it would also be possible to create a feedback loop such that the cavity adjusted its length to optimise the signal for the new wavelength, and recorded the shift in wavelength, thereby giving an absolute determination of the refractive index change.

Refractive index sensors are widely used in many areas of analytical science, particularly as detectors in chromatography and capillary electrophoresis, and for detecting sudden pollution events in water monitoring.

The sensor 1 is a general sensing platform that may be applied for sensing of a wide range of solution-phase and gas-phase analytes. Applications include, without limitation: (i) Environmental sensing, for example monitoring pollutants or other chemical species in rivers or lake water, air quality monitoring; (ii) medicine and healthcare, for example detection of biomarkers in blood, urine, saliva, or breath samples; (iii) process monitoring in a range of industries; (iv) security, for example detection of potentially harmful substances in air or liquid samples; and (v) miniaturised spectrometers, for example as detectors for microfluidic applications or as a more general scientific consumer technology.

The sensor 1 offers considerable opportunities for miniaturisation, with the associated advantages of portability and the extremely small amounts of sample required for analysis. The sensor 1 can be fibre coupled for use in harsh environments or for use in medical endoscopy, and can also be fabricated in arrays in order to carry out parallel analysis, potentially coupling a sensor array to the pixel array of a CCD or CMOS camera for rapid data acquisition. The cavity arrays could also be used in conjunction with engineered receptor arrays for multi-analyte sensing The sensor 1 is also relatively simple compared to most CEAS setups, requiring only a fairly basic light source and detector in place of the sophisticated laser systems and electronics required to run a conventional CEAS measurement.

A third method for active chemical sensing using an optical microcavity is fluorescence sensing. Fluorescence detection of single molecules is relatively routine nowadays, but is limited to molecules that fluoresce brightly with highly efficient electric dipole allowed transitions, and to 'labeled' approaches where non-fluorescent molecules are attached to brightly fluorescent dyes or nanoparticles for sensing purposes. This latter approach requires prior attachment of the label particle before sensing, thus limiting its range of applications. As well as providing the ultimate in sensitivity for chemical sensing applications, single molecule fluorescence is an unparalleled analytic tool for uncovering the dynamics of molecular and nanoscopic systems, as disclosed in Reference [12]

Enhancement of fluorescence due to a microcavity, by the Purcell effect described previously, increases the emission rate at which fluorescence occurs by the Purcell factor $F_P$ of the cavity multiplied by the factor $(1+Q/Q_d)^{-1}$ where $Q_d$ is the quality factor of the emission spectrum.

In doing so it allows control over the direction of emission of the fluorescent radiation since a high $F_P$ encourages emission into the resonant modes at the expense of other off resonance or leaky modes. The result is that the signal reaching a detector can be significantly increased; less expensive optical components are required to collect and direct the emitted light; and single molecule sensing can be achieved more quickly than in the absence of a microcavity. Alternatively the detection of molecules that emit light weakly, for example if a fast competing relaxation process exists, or if the transition is electric dipole forbidden and therefore comparatively slow, may be facilitated, thus increasing the range of molecules that can be detected at the single particle level. Single molecule fluorescence is limited to molecules whose fluorescence quantum yield (QY=the probability of emitting a photon subsequent to excitation) is greater than about 10%, excluding the vast majority of molecules from this technique. In a cavity offering Purcell factor $F_P$ the quantum yield increases to approximately $QY'=F_P \times QY/(1+F_P \times QY)$.

A fourth method for chemical sensing is Raman spectroscopy, where illumination with EM radiation from a laser results in coherent scattering of light at energies lower than that of the illumination as a result of vibrational excitation (Stokes), or higher than that of the illumination as a result of vibrational de-excitation (anti-Stokes). Each molecule has a characteristic vibrational energy spectrum and so the spectrum of the scattered light can be used to indentify the chemical composition of the sample. This technique is widely used as an analytic tool in chemistry and biochemistry, as it is applicable to a large range of chemical species (much larger than fluorescence).

Enhanced Raman spectroscopy is well known and widely used, enabling detection sensitivity at the single molecule level. Enhancement of the Raman signal is most commonly achieved by surface plasmons at a metal interface, in a technique known as Surface Enhanced Raman Scattering (SERS). This is typically a broadband technique in which chemical identification required the use of some spectroscopic tool such as a spectrograph which may be bulky and/or expensive. Resonant cavity enhanced Raman spectroscopy allows selected Raman transitions that are resonant with a high Q cavity mode to be enhanced above others, thereby removing the need for further spectroscopic dispersion of the scattered radiation [13].

The use of the cavities described here for cavity enhanced Raman spectroscopy allows the large field enhancements achieved by the small cavity size to be utilised for strong enhancement of the resonant scattered radiation. The high quality factors possible provide a high degree of spectral resolution in the enhancement of the scattered signal. The tunability of the cavity allows a spectrum to be recorded without recourse to bulky and expensive optical elements. The short cavity lengths and radius of curvature of the concave mirrors provide single mode tuning over a wide spectral range. An additional cavity mode can optionally be used to enhance the excitation radiation intensity, whereby the overall signal enhancement will be the product of the enhancements of the incident and scattered radiation fields. The cavities can be used in conjunction with metal nanoparticles or other nanostructures for plasmonic enhancement of the Raman scattering signal.

As an experimental example, a sensor 1 as described above was used as follows. Initially, the optical cavity 13 was filled with water and then saturated saline solution was injected into the optical cavity 13. During this process, the presence of the salt was measured via a change in refractive index. The difference should be about 0.045 Refractive Index Units (RIU) between pure water and saturated solution.

FIG. 7 is a graph of the results, being a colour-scale plot of the spectrum of light transmitted through the optical cavity 13 against time. The bright line corresponds to high degree of optical transmission through a resonant mode. The time at which the salt solution is injected (about 35 seconds) is indicated by an arrow. As can be seen, the cavity mode is stable until the salt solution arrives, after which the resonance shifts to longer wavelength by about 12 nm. This shows off the sensor 1 operating effectively.

In this example, the cavity mode volume of the optical cavity 13 was of order 1 $\mu m^3$, so the mass of salt being measured at any one time was about 260 fg (i.e. $2.6 \times 10^{-13}$ g)

In this example, the optical cavity 13 achieved measurement of a change in refractive index some 100 times smaller ($\sim 5 \times 10^{-4}$ RIU) than the line width of the resonance. With refinement of the optical cavity 13, it is anticipated that this may be improved further perhaps up to about 100 times better, which in turn suggests an ability to detect as little as ~10 ag of salt, equating to less than a million molecules. It is reasonable to expect similar sensitivities from other impurities.

The relatively slow time scale of the data shown in FIG. 7 is indicative of the gradual change in the salt concentration in the optical cavity 13. A better design of fluidics system for injecting the salt would speed up these changes.

REFERENCES

[1] M. Trupke, E. A. Hinds, S. Eriksson, E. A. Curtis, Z. Moktadir, E. Kukharenka, and M. Kraft, Appl Phys Lett 89, 211106 (2005)
[2] M. Trupke, J. Goldwin, B. Darquie, G. Dutier, S. Eriksson, J. Ashmore, and E. A. Hinds, Phys Rev Lett 99, 063601 (2007)
[3] T. Steinmetz, Y. Colombe, D. Hunger, T. W. Hansch, A. Balocchi, R. J. Warburton, and J. Reichel, Appl Phys Lett 89, 111110 (2006)
[4] G. Cui, J. M. Hannigan, R. Loeckenhoff, F. M. Matinaga, M. G. Raymer, S. Bhongale, M. Holland, S. Mosor, S. Chatterjee, H. M. Gibbs, and G. Khitrova, Optics Express 14, 2291 (2006)
[5] D Hunger et al, NJP 12, 065038 (2010)
[6] Dolan et al., "Femtoliter tunable optical cavity arrays", Optics Letters, Vol. 35, No. 21, November 2010
[7] G. Berden, R. Peeters and G. Meijer, *Int. Rev. Phys. Chem.*, 19(4) 565 (2000)
[8] J. J. Scherer, J. B. Paul, A. O'Keefeand and R. J. Saykally, *Chem. Rev.*, 97(1) 25 (1997)
[9] M. D. Wheeler, S. M. Newman, A. J. Orr-Ewing and M. N. R. Ashfold, *J. Chem. Soc., Faraday Trans.*, 94(3) 337 (1998)
[10] S. M. Ball and R. L. Jones, *Chem. Rev.*, 103(12) 5239 (2003); D. B. Atkinson, *Analyst*, 128(2) 117 (2003);
[11] S. S. Brown, *Chem. Rev.*, 103 5219 (2003).
[12] Chris Gell et al, Handbook of Single Molecule fluorescence spectroscopy (OUP, 2006)
[13] William M Tong et al, U.S. Pat. No. 7,511,808 (2009).

The invention claimed is:
1. A method of sensing an analyte in a chemical sample, the method comprising:
  providing a pair of mirrors opposed along an optical axis, at least one of the mirrors being concave and having a radius of curvature of at most 50 μm, the mirrors being shaped to provide an optical cavity with stable resonance in at least one mode and having a cavity length of at most 50 μm;

further providing an actuator system arranged to move the mirrors relative to each other along the length of the optical cavity for tuning a wavelength of the at least one mode of said cavity;

introducing a chemical sample inside the optical cavity;

illuminating the cavity with electromagnetic radiation capable of interacting with the chemical sample;

detecting the electromagnetic radiation emitted from the optical cavity;

tuning the wavelength of said at least one mode of said cavity using the actuator system to match an absorption wavelength of said analyte; and analysing the detected electromagnetic radiation to detect a reduction in the detected electromagnetic radiation that is indicative of the presence of said analyte.

2. The method according to claim 1, wherein said at least one mode is confined perpendicular to the optical axis between the mirrors.

3. The method according to claim 1, wherein the radius of curvature of said at least one of the mirrors that is concave is at most 30 μm.

4. The method according to claim 1, wherein the mirrors have respective radii of curvature $\beta$ and $\gamma$ meeting the requirement that $0 \leq (1-(L/\beta)) \cdot (1-(L/\gamma)) \leq 1$, where L is a length of the optical cavity.

5. The method according to claim 1, wherein one of the mirrors is planar.

6. The method according to claim 1, wherein the at least one of the mirrors that is concave is formed by focussed ion beam milling.

7. The method according to claim 1, wherein said at least one mode includes a fundamental transverse mode of the optical cavity.

8. The method according to claim 1, wherein the chemical sample is a gas or liquid sample.

9. The method according to claim 1, wherein the cavity length is at most 30 μm.

10. The method according to claim 1, wherein the mirrors have a root-mean-square roughness of at most 1 nm.

11. The method according to claim 1, wherein the mirrors have a reflectance of at least 99%.

12. The method according to claim 1, wherein the mirrors are Bragg reflectors.

13. The method according to claim 1, wherein the optical cavity has a single mode within a band of wavelengths of the electromagnetic radiation.

14. The method according to claim 1, wherein the actuation system comprises a piezoelectric actuator.

15. A sensor comprising:

a pair of mirrors opposed along an optical axis, at least one of the mirrors being concave and having a radius of curvature of at most 50 μm, the mirrors being shaped to provide an optical cavity with stable resonance in at least one mode and having a cavity length of at most 50 μm;

an actuator system arranged to move the mirrors relative to each other along the length of the optical cavity for tuning a wavelength of the at least one mode of said cavity, wherein the actuator system is arranged to tune the wavelength of said at least one mode of said cavity to match an absorption wavelength of an analyte in a chemical sample;

a sample introduction system arranged to introduce the chemical sample inside the optical cavity;

an electromagnetic radiation source arranged to illuminate the cavity with electromagnetic radiation capable of interacting with the chemical sample;

a detector arranged to detect the electromagnetic radiation emitted from the optical cavity; and an analysis unit arranged to detect a reduction in the detected electromagnetic radiation that is indicative of the presence of said analyte.

16. A method of sensing an analyte in a chemical sample, the method comprising:

providing a pair of mirrors opposed along an optical axis, at least one of the mirrors being concave and having a radius of curvature of at most 50 μm, the mirrors being shaped to provide an optical cavity with stable resonance in at least one mode and having a cavity length of at most 50 μm;

further providing an actuator system arranged to move the mirrors relative to each other along the length of the optical cavity for tuning a wavelength of the at least one mode of said cavity;

introducing a chemical sample inside the optical cavity;

illuminating the cavity with electromagnetic radiation capable of interacting with the chemical sample;

detecting the electromagnetic radiation emitted from the optical cavity;

analysing the detected electromagnetic radiation to detect a change in the refractive index of the chemical sample within the optical cavity that is indicative of the analyte.

17. The method according to claim 16, wherein said at least one mode is confined perpendicular to the optical axis between the mirrors.

18. The method according to claim 16, wherein said at least one of the mirrors that is concave has a radius of curvature of at most 30 μm.

19. The method according to claim 16, wherein the mirrors have respective radii of curvature $\beta$ and $\gamma$ meeting the requirement that $0 \leq (1-(L/\beta)) \cdot (1-(L/\gamma)) \leq 1$, where L is the length of the optical cavity.

20. The method according to claim 16, wherein one of the mirrors is planar.

21. The method according to claim 16, wherein the at least one of the mirrors that is concave is formed by focussed ion beam milling.

22. The method according to claim 16, wherein said at least one mode includes a fundamental transverse mode of the optical cavity.

23. The method according to claim 16, wherein the chemical sample is a gas or liquid sample.

24. The method according to claim 16, wherein the cavity length is at most 30 μm.

25. The method according to claim 16, wherein the mirrors have a root-mean-square roughness of at most 1 nm.

26. The method according to claim 16, wherein the mirrors have a reflectance of at least 99%.

27. The method according to claim 16, wherein the mirrors are Bragg reflectors.

28. The method according to claim 16, wherein the optical cavity has a single mode within a band of wavelengths of the electromagnetic radiation.

29. The method according to claim 16, wherein the actuation system comprises a piezoelectric actuator.

30. A sensor comprising:

a pair of mirrors opposed along an optical axis, at least one of the mirrors being concave and having a radius of curvature of at most 50 μm, the mirrors being shaped to provide an optical cavity with stable resonance in at least one mode and having a cavity length of at most 50 µm;

an actuator system arranged to move the mirrors relative to each other along the length of the optical cavity for tuning a wavelength of the at least one mode of said cavity;

a sample introduction system arranged to introduce a chemical sample inside the optical cavity;

an electromagnetic radiation source arranged to illuminate the cavity with electromagnetic radiation capable of interacting with the chemical sample;

a detector arranged to detect the electromagnetic radiation emitted from the optical cavity; and an analysis unit arranged to analyse the detected electromagnetic radiation to detect a change in the refractive index of the chemical sample within the optical cavity that is indicative of an analyte in the chemical sample.

* * * * *